(12) United States Patent
Pu et al.

(10) Patent No.: US 8,200,319 B2
(45) Date of Patent: Jun. 12, 2012

(54) LOCATING FIDUCIAL POINTS IN A PHYSIOLOGICAL SIGNAL

(75) Inventors: Yachuan Pu, Dana Point, CA (US); Charles Gropper, Mission Viejo, CA (US); Dongping Lin, Irvine, CA (US)

(73) Assignee: CardioNet, Inc., Conshohocken, PA (US)

( * ) Notice: Subject to any disclaimer, the term of this patent is extended or adjusted under 35 U.S.C. 154(b) by 646 days.

(21) Appl. No.: 12/368,976

(22) Filed: Feb. 10, 2009

(65) Prior Publication Data

US 2010/0204599 A1 Aug. 12, 2010

(51) Int. Cl.
*A61B 5/0402* (2006.01)
(52) U.S. Cl. ........................................ 600/509
(58) Field of Classification Search ............. 607/509, 607/512, 515, 517, 521
See application file for complete search history.

(56) References Cited

U.S. PATENT DOCUMENTS

| | | | |
|---|---|---|---|
| 4,622,979 A | 11/1986 | Katchis et al. |
| 4,630,204 A | 12/1986 | Mortara |
| 4,646,754 A | 3/1987 | Seale |
| 4,920,489 A | 4/1990 | Hubelbank et al. |
| 4,938,228 A | 7/1990 | Righter et al. |
| 4,951,681 A | 8/1990 | Mortara |
| 4,958,641 A | 9/1990 | Digby et al. |
| 4,977,899 A | 12/1990 | Digby et al. |
| 5,047,930 A | 9/1991 | Martens et al. |
| D326,716 S | 6/1992 | Mortara |
| 5,191,891 A | 3/1993 | Righter |
| 5,197,479 A | 3/1993 | Hubelbank et al. |
| 5,226,425 A | 7/1993 | Righter |
| 5,299,118 A | 3/1994 | Martens et al. |
| RE34,663 E | 7/1994 | Seale |
| 5,365,935 A | 11/1994 | Righter et al. |
| 5,421,342 A | 6/1995 | Mortara |
| 5,490,515 A | 2/1996 | Mortara |
| 5,522,393 A | 6/1996 | Phillips et al. |
| 5,522,396 A | 6/1996 | Langer et al. |
| 5,546,950 A | 8/1996 | Schoeckert et al. |
| 5,560,367 A | 10/1996 | Haardt et al. |
| 5,581,369 A | 12/1996 | Righter et al. |
| 5,596,993 A | 1/1997 | Oriol et al. |

(Continued)

FOREIGN PATENT DOCUMENTS

CN 2569743 Y 9/2003

(Continued)

OTHER PUBLICATIONS

Almeida R et al., "Automatic Multilead VCG Based Approach for QT Interval Measurement" Computers in Cardiology 2006 33:369-372.

(Continued)

*Primary Examiner* — Scott Getzow
*Assistant Examiner* — Amanda Patton
(74) *Attorney, Agent, or Firm* — Fish & Richardson P.C.

(57) ABSTRACT

Systems, devices, methods, and techniques relating to the identification of fiducial points. In one aspect, a machine implemented method includes obtaining a first time varying physiological signal and a second time varying physiological signal that relate to biological activity of an organism, the first time varying physiological signal and the second time varying physiological signal forming an analytic pair wherein the analytic pair has a time varying phase angle, defining a reference line by a lower boundary of a representation of the time varying phase angle with respect to a time period, and identifying a fiducial point based on the reference line.

37 Claims, 5 Drawing Sheets

U.S. PATENT DOCUMENTS

| | | | |
|---|---|---|---|
| D377,983 S | 2/1997 | Sabri |
| 5,609,158 A | 3/1997 | Chan |
| 5,634,468 A | 6/1997 | Platt et al. |
| 5,645,069 A | 7/1997 | Lee |
| 5,678,562 A | 10/1997 | Sellers |
| 5,704,351 A | 1/1998 | Mortara et al. |
| 5,730,143 A | 3/1998 | Schwarzberg |
| 5,810,014 A | 9/1998 | Davis et al. |
| 5,827,195 A | 10/1998 | Lander |
| 5,921,937 A | 7/1999 | Davis et al. |
| 5,931,791 A | 8/1999 | Saltzstein et al. |
| 5,957,855 A | 9/1999 | Oriol et al. |
| D414,870 S | 10/1999 | Saltzstein et al. |
| 5,966,692 A | 10/1999 | Langer et al. |
| 6,024,701 A | 2/2000 | Almog |
| 6,028,428 A | 2/2000 | Cunningham et al. |
| 6,069,975 A | 5/2000 | Lehmann et al. |
| 6,076,015 A | 6/2000 | Hartley et al. |
| 6,102,856 A | 8/2000 | Groff et al. |
| 6,161,042 A | 12/2000 | Hartley et al. |
| 6,216,031 B1 | 4/2001 | Findeis et al. |
| 6,269,263 B1 | 7/2001 | Ohnishi et al. |
| 6,278,961 B1 | 8/2001 | Kadtke et al. |
| 6,287,252 B1 | 9/2001 | Lugo |
| 6,340,346 B1 | 1/2002 | Almog et al. |
| 6,366,871 B1 | 4/2002 | Geva |
| 6,368,283 B1 | 4/2002 | Xu et al. |
| 6,370,437 B1 | 4/2002 | Carter et al. |
| 6,377,843 B1 | 4/2002 | Naydenov et al. |
| 6,381,559 B1 | 4/2002 | Huang |
| 6,400,996 B1 | 6/2002 | Hoffberg et al. |
| 6,401,057 B1 | 6/2002 | Kadtke et al. |
| 6,442,421 B1 | 8/2002 | Le Van Quyen et al. |
| 6,463,326 B1 | 10/2002 | Hartley et al. |
| 6,507,749 B1 | 1/2003 | Macgowan et al. |
| 6,507,754 B2 | 1/2003 | Le Van Quyen et al. |
| 6,537,233 B1 | 3/2003 | Rangayyan et al. |
| 6,561,986 B2 | 5/2003 | Baura et al. |
| 6,564,077 B2 | 5/2003 | Mortara |
| 6,564,176 B2 | 5/2003 | Kadtke et al. |
| 6,569,101 B2 | 5/2003 | Quistgaard et al. |
| 6,640,145 B2 | 10/2003 | Hoffberg et al. |
| 6,651,025 B1 | 11/2003 | Drepper |
| 6,697,655 B2 | 2/2004 | Sueppel et al. |
| 6,728,691 B1 | 4/2004 | Neuneier et al. |
| 6,731,990 B1 | 5/2004 | Carter et al. |
| 6,732,064 B1 | 5/2004 | Kadtke et al. |
| 6,735,466 B1 | 5/2004 | Haghighi-Mood |
| 6,738,734 B1 | 5/2004 | Huang |
| 6,950,702 B2 | 9/2005 | Sweeney |
| 6,996,261 B2 | 2/2006 | deCharms |
| 7,311,665 B2 | 12/2007 | Hawthorne et al. |
| 7,542,878 B2 | 6/2009 | Nanikashvili |
| 2001/0014776 A1 | 8/2001 | Oriol et al. |
| 2002/0095099 A1 | 7/2002 | Quyen et al. |
| 2002/0128804 A1 | 9/2002 | Geva |
| 2003/0009399 A1 | 1/2003 | Boerner |
| 2003/0028442 A1 | 2/2003 | Wagstaff et al. |
| 2003/0065633 A1 | 4/2003 | Neuneier et al. |
| 2003/0069486 A1 | 4/2003 | Sueppel et al. |
| 2003/0069487 A1 | 4/2003 | Mortara |
| 2003/0105499 A1 | 6/2003 | Hartley et al. |
| 2003/0166995 A1 | 9/2003 | Jansen |
| 2003/0233050 A1 | 12/2003 | Haghighi-Mood et al. |
| 2004/0010201 A1 | 1/2004 | Korzinov et al. |
| 2004/0260169 A1 | 12/2004 | Sternnickel |
| 2005/0119833 A1 | 6/2005 | Nanikashvili |
| 2005/0203349 A1 | 9/2005 | Nanikashvili |
| 2006/0084881 A1 | 4/2006 | Korzinov et al. |
| 2006/0122525 A1 | 6/2006 | Shusterman |
| 2007/0100213 A1 | 5/2007 | Dossas et al. |
| 2007/0219453 A1* | 9/2007 | Kremliovsky et al. ....... 600/509 |
| 2008/0146954 A1 | 6/2008 | Bojovic et al. |
| 2009/0088655 A1 | 4/2009 | Vajdic et al. |

FOREIGN PATENT DOCUMENTS

| | | |
|---|---|---|
| WO | WO03/071945 | 9/2003 |
| WO | WO2005/072607 | 8/2005 |
| WO | WO2006/044919 | 4/2006 |
| WO | WO2008/085179 | 7/2008 |

OTHER PUBLICATIONS

Benitez, D. et al. "The Use of the Hilbert Transform in ECG Signal and Analysis" Computers in Biology and Medicine 31 (2001) 399-406.

Bennet, Bill, Attorney for Pizzeys, in Australian Patent Application No. 2005295313, International Filing Date of Oct. 18, 2005, response filed on May 27, 2009, 25 pages.

Bhattacharya et al., "Universality in the brain while listening to music," Apr. 2001, Proceedings Royal Society London B., 268:2423-2433, 11 pages.

Bortolan G., "Algorithmic Testing for QT Interval Measurements" Computers in Cardiology 2006 33:365-368.

Bray et al., Use of Topological Charge to Determine Filament Location and Dynamics in a Numerical Model of Scroll Wave Activity, IEEE Transactions on Biomedical Engineering 49(10):1086-1093 (Oct. 2002), 8 pages.

Braymore, Bryon, Patent Examiner, Canadian Patent Office, Application No. 2,584,503, in Office Action dated Feb. 16, 2009, 6 pages.

Chen X et al., "Reliable Automated QT Interval Measurement for Clinical Evaluation" Computers in Cardiology 2006 33:373-376.

Chesnokov Yv et al., "Individually Adaptable Automatic QT Detector" Computers in Cardiology 2006 33:337-340.

Christov II et al., "Fully Automated Method for QT Interval Measurement in ECG" Computers in Cardiology 2006 33:321-324.

Chudacek V et al., "Automatic QT Interval Measurement Using a Rule-Based Gradient Method" Computers in Cardiology 2006 33:349-351.

Clifford GD et al., "Model-Based Determination of QT Intervals" Computers in Cardiology 2006 33:357-360.

Coast, D.A., et al., "An Approach to Cardiac Arrhythmia Analysis using Hidden Markov Models", Biomedical Engineering, IEEE Transactions on ,vol. 37, Issue 9, Sep. 1990 pp. 826-836.

Daskalov, I. K., et al., "Automatic Detection of the Electrocardiogram T-Wave End", Medical & Biological Engineering & Computing, vol. 37, Issue 3, May 1999, pp. 348-353.

Daskalov, I. K., et al., "Electrocardiogram Signal Preprocessing for Automatic Detection of QRS Boundaries" , Medical Engineering & Physics 21, 1999, pp. 37-44.

Electronic Records Administration, in Australian Patent Application Serial No. 2005295313, filed Oct. 18, 2005, Notice of Acceptance, mailed Dec. 10, 2009, 3 pages, to be published by the USPTO.

Forward, Matthew, Examiner, Australian Government IP Australia, Examination Report, mailed Sep. 15, 2008, 3 pages.

Forward, M., Examiner, Australian Government IP Australia, in Australian Patent Application No. 2005295313, Examination Report dated Aug. 7, 2009, 2 pages (to be published by the USPTO).

Getzow, Scott M., International Search Report and Written Opinion mailed May 19, 2006 in PCT Application No. PCT/US05/37492, which corresponds to U.S. Appl. No. 11/081,401, to be published by the U.S. Patent and Trademark Office (8 pages).

Goldberger, A. L, "Bhargava V: QRS Duration Measurement Using High-Frequency Electrocardiography: Applications and Limitations of a new Technique", Computers and Biomedical Research, vol. 15, Issue 5 , Oct. 1982, pp. 475-484.

Gritzali, F. et al., "Detection of the P and T waves in an ECG", Computers and Biomedical Research, vol. 22, Issue 1 , Feb. 1989, pp. 83-91.

Hamilton, P.S. et al., "Quantitative Investigation of QRS Detection Rules using the MIT-BIH Arrhythmia Database", IEEE Transactions on Biomedical Engineering 1986, BME-33, pp. 1157-1187.

Haykin, S., Editor, "Nonlinear Methods of Spectral Analysis", Topics in Applied Physics, vol. 34, Springer-Verlag, 1979.

Hayn D "Automated QT Interval Measurement from Multilead ECG Signals" Computers in Cardiology 2006 33:381-384.

Hunter, William E., Attorney for Fish & Richardson, in Canadian Patent Application No. 2,584,503, International Filing Date of Oct.

18, 2005, instructions to Foreign Associate for response to Office Action dated Mar. 24, 2009, 12 pages. (to be published by the USPTO).

Jeekai & Partners, Translation of Office Action mailed May 23, 2008 in Chinese Patent Application No. 2005-80040134.5, which corresponds to U.S. Appl. No. 11/081,401, to be published by the U.S. Patent and Trademark Office (11 pages).

Kay, S. M. et al., "Spectrum Analysis—A Modern Perspective", Proceedings of the IEEE, vol. 69, No. 11, Nov. 1981.

Kemmelings, J. G. et al., "Automatic QRS Onset and Offset Detection for Body Surface QRS Integral Mapping of Ventricular Tachycardia", Biomedical Engineering, IEEE Transactions on, vol. 41, Issue 9, Sep. 1994 pp. 830-836.

Laguna, P. et al., "Automatic Detection of Wave Boundaries in Multilead ECG Signals: Validation with the CSE Database", Computers and Biomedical Research, vol. 27, Issue 1 , Feb. 1994, pp. 45-60.

Laguna, P. et al., "New Algorithm for QT Interval Analysis In 24-Hour Holter ECG: Performance And Applications", Med Biol Eng Comput. Jan. 1990;28(1), pp. 67-73.

Langley P et al., "Fully Automated Computer Measurement of QT Interval from the 12-Lead Electrocardiogram" Computers in Cardiology 2006 33:345-348.

Li, C. et al., "Detection of ECG Characteristic Points Using Wavelet Transforms", Biomedical Engineering, IEEE Transactions on vol. 42, Issue 1, Jan. 1995 pp. 21-28.

Martinez JP et al., "Stability of QT Measurements in the PTB Database Depending on the Selected Lead" Computers in Cardiology 2006 33:341-344.

McLaughlin et al "Comparison of Automatic QT Measurement Techniques in the Normal 12 Lead Electrocardiogram" Br Heart 1995; 74:84-89.

Mensing S et al., "Identifying and Measuring Representative QT Intervals in Predominantly Non-Normal ECGs" Computers in Cardiology 2006 33:361-364.

Meyer, C. R. et al., "Electrocardiogram baseline noise estimation and removal using cubic splines and state-space computation techniques", Computers and Biomedical Research, vol. 10, pp. 459-470, 1977.

Meyer, M. et al., "Stability of Heartbeat Interval Distributions in Chronic High Altitude Hypoxia," Oct.-Dec. 1998, Intergrative Physiological and Behavioral Science, 33(4):344 362, 19 pages.

Mneimneh Ma et al., "Integrative Technique for the Determination of QT Interval" Computers in Cardiology 2006 33:329-332.

Moody GB et al., "The PhysioNet / Computers in Cardiology Challenge 2006: QT Interval Measurement" Computers in Cardiology 2006 33:313-316.

Plonsey, R., et al., "Bioelectricity: A Quantitative Approach" (Hardcover—Nov. 30, 2000) p. 273 and p. 286.

Povinelli RJ et al., "Cardiac Model Based Approach to QT Estimation" Computers in Cardiology 2006 33:333-336.

"The QT Interval" 12-Lead ECG's—A "Web Brain" for Easy Interpretation, http://medinfo.ufl.edu/~ekg/QT%20interval.html.

Rao, B. D. et al., "Model based Processing of Signals: A State Space Approach", Proc. IEEE, vol. 80, pp. 283-309, Feb. 1992.

Schneider R et al., "Challenge 2006: QT Interval Measurement" Computers in Cardiology 2006 33:325-328.

Signal Processing and Simulation Newsletter, "Hilbert Transform, Analytic Signal and the Complex Envelope", http://www.complextoreal.com/tcompelx.html.

Song-Kai et al., "The Real-Time Detection of QRS-Complex using the Envelop of ECG", IEEE Engineering in Medicine and Biology Society, 10$^{th}$ Annual International Conference, 1988, 1 page.

Sun, Yan et al., "Characteristic Wave Detection in ECG Signal Using Morphological Transform", BMC Cardiovascular Disorders (http://www.biomedcentral.com/content/pdf/1471-2261-5-28.pdf), Sep. 2005, pp. 1-7.

Thrane, N., Ph.D., "The Hilbert Transform", in Technical Review No. 3—1984.

Tironi DA et al., "Automated QT Interval Analysis on Diagnostic Electrocardiograms" Computers in Cardiology 2006 33:353-356.

Weber, Myriam, Authorized Officer, European Patent Office, in International Application No. PCT/US2007/063916, International Search Report, mailed Apr. 3, 2008, 16 pages, (to be published by the USPTO).

Willems, J. L.., et al., "Influence Of Noise on Wave Boundary Recognition by ECG Measurement Programs. Recommendations for Preprocessing", Computers and Biomedical Research vol. 20, Issue 6, Dec. 1987, pp. 543-562.

Wu CY et al., "A Semi-Automatic QT Interval Measurement Based on Digital Filters" Computers in Cardiology 2006 33:317-320.

Xue, Q et al "Algorithms for Computerized QT Analysis" J. of Electrocardiology vol. 30; pp. 181-186.

Xue JQ, "QT Interval Measurement: What Can We Really Expect?" Computers in Cardiology 2006 33:385-388.

Zong W et al.. "A QT Interval Detection Algorithm Based on ECG Curve Length Transform" Computers in Cardiology 2006 33:377-380.

Biomedical Computer Laboratory, Institute for Biomedical Computing, Washington University, "Progress Report No. 21," Jul. 1, 1984-Jun. 30, 1985, 164 pages.

Savi Wireless—Mobile Cardiac Telemetry Brochure, published by at least May 2009, 12 pages, Medicomp, Melbourne, Florida.

Authorized agent Blaine R. Copenheaver, International Search Report/Written Opinion in International Application No. PCT/US2010/023667 mailed Apr. 16, 2010, 10 pages.

* cited by examiner

LOCATING FIDUCIAL POINTS IN A PHYSIOLOGICAL SIGNAL

BACKGROUND

The electrical activity of various organs, such as the heart or brain, can be monitored, and this electrical activity can be analyzed to look for patterns that may assist in diagnosing various conditions. For example, the electrical activity of the heart can be monitored to track various aspects of the functioning of the heart. Given the volume conductivity of the body, electrodes on the body surface or beneath the skin can display potential differences related to this activity. Anomalous electrical activity can be indicative of disease states or other physiological conditions ranging from benign to fatal.

Cardiac monitoring devices can sense the cardiac electrical activity of a living being and identify heart beats. Frequently, identification of heart beats is performed by identifying various portions of the cardiac cycle as can be seen in an electrocardiogram (ECG). Various identifiers, such as P, Q, R, S and T, are typically assigned to various deflections in the ECG signal. Many techniques have been developed for analyzing ECG signals, but further improvements are desirable.

SUMMARY

The present application describes systems and techniques relating to automated analysis of a physiological signal or signals of an organism, such as a cardiac signal. Automated analysis of a cardiac signal or signals can include, for example, identifying a reference line such as an isoelectric; locating fiducial points such as a P-wave onset, a P-wave offset, a T-wave onset, a T-wave offset, a Q-point, an R-point, and an S-point; and/or detecting a physiological condition.

In a first aspect, a machine implemented method includes obtaining a first time varying physiological signal and a second time varying physiological signal that relate to biological activity of an organism, the first time varying physiological signal and the second time varying physiological signal forming an analytic pair wherein the analytic pair has a time varying phase angle. The method further includes defining a reference line by a boundary of a representation of the time varying phase angle with respect to a time period. The method further includes identifying a fiducial point based on the reference line.

Implementations can include any, all, or none of the following features. The machine implemented method can include approximating the time varying phase angle, wherein the approximation of the varying phase angle $\phi_{\Delta \vec{A}(t_{i+K})}$ can be defined by the function:

$$\varphi_{\Delta \vec{A}(t_{i+K})} \approx \frac{imag[\Delta \vec{A}(t_{i+K})]}{|\Delta \vec{A}(t_{i+K})|} = \frac{\hat{x}(t_{i+K}) - \hat{x}(t_i)}{\sqrt{(x(t_{i+K}) - x(t_i))^2 + (\hat{x}(t_{i+K}) - \hat{x}(t_i))^2}}$$

where x(t) includes the first time varying physiological signal and $\hat{x}$(t) includes the second time varying physiological signal, x(t) and $\hat{x}$(t) forming the analytic pair $\vec{A}$(t); where i is a current sample; where K is K samples away; and where $\Delta \vec{A}(t_{i+k})$ is the change of the two vectors ((x($t_i$), $\hat{x}$($t_i$)) and (x($t_{i+K}$), $\hat{x}$($t_{i+K}$)). The reference line can include an isoelectric line defined by a lower boundary of the representation of the time varying phase angle. The machine implemented method can include calculating a corresponding function to a downslope or an upslope of the representation of the time varying phase angle within the time period; and wherein identifying a fiducial point based on the reference line can include identifying a fiducial point based on an intersection of the corresponding function and the reference line. Calculating a corresponding function to a downslope of the representation of the time varying phase angle can include calculating a tangent line where the downslope can have a minimum slope.

Calculating a corresponding function to an upslope of the representation of the time varying phase angle can include calculating a tangent line where the upslope has a maximum slope. Also, identifying a fiducial point based on an intersection of the corresponding function and the reference line can include offsetting the intersection by a constant. Furthermore, calculating a corresponding function to a downslope or an upslope of the representation of the time varying phase angle can include calculating the regression line of the downslope or the upslope of the representation of the time varying phase angle within the time period. The machine implemented can include applying a trigonometric function to the time varying phase angle to create the representation. Obtaining a first time varying physiological signal can include obtaining a sensed signal x(t); and wherein obtaining a second time varying physiological signal $\hat{x}$(t) can include obtaining a transformation of x(t) to form the analytic pair $\vec{A}$(t). Obtaining a transformation of x(t) can include obtaining a Hilbert Transformation H(x(t)) of the first time varying physiological signal. Also, obtaining a transformation of x(t) can include obtaining a derivative of x(t). Obtaining a first time varying physiological signal can include obtaining a first sensed signal based on a first lead configuration; wherein obtaining a second time varying physiological signal can include obtaining a second sensed signal based on a second lead configuration wherein the second sensed signal can be orthogonal to the first; and wherein obtaining the first and second time varying physiological signals can include obtaining the signals from a data storage device. Also, identifying a fiducial point can include identifying one of a T-wave offset, T-wave onset, P-wave offset, P-wave onset, Q-point, R-point, and S-point.

In other aspects, a system can include one or more computers, and a computer-readable storage device having a computer program product encoded therein, the computer program product operable to cause the one or more computers to perform operations which can include: obtaining a first time varying physiological signal and a second time varying physiological signal that relate to biological activity of an organism, the first time varying physiological signal and the second time varying physiological signal forming an analytic pair wherein the analytic pair has a time varying phase angle; defining a reference line by a boundary of a representation of the time varying phase angle with respect to a time period; and identifying a fiducial point based on the reference line.

Implementations can include any, all, or none of the following features. The computer-readable storage device can be further operable to cause the one or more computers to perform operations including: calculating a corresponding function to a downslope or an upslope of the representation of the time varying phase angle within the time period; and wherein identifying a fiducial point based on the reference line can include identifying a fiducial point based on an intersection of the corresponding function and the reference line. Calculating a corresponding function to a downslope or an upslope of the representation of the time varying phase angle can include calculating one of a tangent line, a regression line, and a least square approximation to the downslope or the upslope. Identifying a fiducial point based on an intersection of the corresponding function and the reference line can include offsetting the intersection by a constant. The computer-readable storage device can be further operable to cause the one or more computers to perform operations including applying a trigonometric function to the time varying phase angle to create the representation. The computer-readable storage device can be further operable to cause the one or more computers to perform operations can include approximating the time varying phase angle, wherein the approximation of the varying phase angle $\varphi_{\Delta \vec{A}(t_{i+K})}$ can be defined by the function:

$$\varphi_{\Delta \vec{A}(t_{i+K})} \approx \frac{imag[\Delta \vec{A}(t_{i+K})]}{|\Delta \vec{A}(t_{i+K})|} = \frac{\hat{x}(t_{i+K}) - \hat{x}(t_i)}{\sqrt{(x(t_{i+K}) - x(t_i))^2 + (\hat{x}(t_{i+K}) - \hat{x}(t_i))^2}}$$

where x(t) includes the first time varying physiological signal and x̂(t) includes the second time varying physiological signal, x(t) and x̂(t) forming the analytic pair $\vec{A}(t)$; where i can be a current sample; where K can be K samples away; and where $\Delta \vec{A}(t_{i+k})$ is the change of the two vectors ((x(t$_i$), x̂(t$_i$)) and (x(t$_{i+K}$), x̂(t$_{i+K}$))). Obtaining a first time varying physiological signal can include obtaining a sensed signal x(t); and wherein obtaining a second time varying physiological signal x̂(t) can include obtaining a transformation of x(t) to form the analytic pair $\vec{A}(t)$. Obtaining a transformation of x(t) can include obtaining a Hilbert Transformation H(x(t)) of the first time varying physiological signal. Obtaining a transformation of x(t) can include obtaining a derivative of x(t). Obtaining a first time varying physiological signal can include obtaining a first sensed signal based on a first lead configuration; wherein obtaining a second time varying physiological signal can include obtaining a second sensed signal based on a second lead configuration wherein the second sensed signal can be orthogonal to the first; and wherein obtaining the first and second time varying physiological signals can include obtaining the signals from a data storage device. Identifying a fiducial point can include identifying one of a T-wave offset, T-wave onset, P-wave offset, P-wave onset, Q-point, R-point, and S-point.

In other aspects, an apparatus can include circuitry operable to obtain a first time varying physiological signal and a second time varying physiological signal that relate to biological activity of an organism, the first time varying physiological signal and the second time varying physiological signal forming an analytic pair wherein the analytic pair has a time varying phase angle; circuitry operable to define a reference line by a boundary of a representation of the time varying phase angle with respect to a time period; and circuitry operable to identify a fiducial point based on the reference line.

Implementations can include any, all, or none of the following features. The apparatus can include circuitry operable to transmit the identified fiducial points. The apparatus can include circuitry operable to calculate a corresponding function to a downslope or an upslope of the representation of the time varying phase angle within the time period; and wherein the circuitry operable to identify a fiducial point is further operable to identify a fiducial point based on an intersection of the corresponding function and the reference line. The circuitry operable to calculate a corresponding function to a downslope or an upslope of the representation of the time varying phase angle can be further operable to calculate one of a tangent line, a regression line, and a least square approximation to the downslope or the upslope. The circuitry operable to identify a fiducial point based on an intersection of the corresponding function and the reference line can be further operable to offset the intersection by a constant. The apparatus can include circuitry operable to approximate the time varying phase angle, wherein the approximation of the varying phase angle $\varphi_{\Delta \vec{A}(t_{i+K})}$ can be defined by the function: $$\varphi_{\Delta \vec{A}(t_{i+K})} \approx \frac{imag[\Delta \vec{A}(t_{i+K})]}{|\Delta \vec{A}(t_{i+K})|} = \frac{\hat{x}(t_{i+K}) - \hat{x}(t_i)}{\sqrt{(x(t_{i+K}) - x(t_i))^2 + (\hat{x}(t_{i+K}) - \hat{x}(t_i))^2}}$$

where x(t) includes the first time varying physiological signal and x̂(t) includes the second time varying physiological signal, x(t) and x̂(t) forming the analytic pair $\vec{A}(t)$; where i is a current sample; where K is K samples away; and where $\Delta \vec{A}(t_{i+k})$ is the change of the two vectors ((x(t$_i$), x̂(t$_i$)) and (x(t$_{i+K}$), x̂(t$_{i+K}$))). The apparatus can include circuitry operable to apply a trigonometric function to the time varying phase angle to create the representation. The circuitry operable to obtain a first time varying physiological signal can be further operable to obtain a sensed signal x(t); and wherein the circuitry, operable to obtain a second time varying physiological signal, x̂(t) can be further operable to obtain a transformation of x(t) to form the analytic pair $\vec{A}(t)$. The circuitry operable to obtain a transformation of x(t) can be further operable to obtain a Hilbert Transformation H(x(t)) of the first time varying physiological signal. The circuitry operable to obtain a transformation of x(t) can include obtaining a derivative of x(t).

The circuitry operable to obtain a first time varying physiological signal can be further operable to obtain a first sensed signal based on a first lead configuration; wherein the circuitry operable to obtain a second time varying physiological signal can be further operable to obtain a second sensed signal based on a second lead configuration wherein the second sensed signal can be orthogonal to the first; and wherein the circuitry operable to obtain the first and second time varying physiological signals can be further operable to obtain the signals from a data storage device. The circuitry operable to identify a fiducial point can be further operable to identify one of a T-wave offset, T-wave onset, P-wave offset, P-wave onset, Q-point, R-point, and S-point.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

The present application describes systems and techniques relating to automated analysis of a physiological signal of an organism, including identification of a reference line such as an isoelectric line and identification of fiducial points for such a physiological signal. The physiological signal can be a cardiac signal, such as an ECG signal, a brain signal, such as an electroencephalogram (EEG) signal, a respiratory signal, a blood pressure signal, or other signals from an organism. The signal(s) can be obtained directly, for example by monitoring heart activity of a human patient as described further below, or the signal(s) can be obtained indirectly from another device or system. For example, the signal processing and analysis described herein can be performed in real-time as the signals are acquired and/or on stored signals retrieved from a database or other electronic storage devices.

The systems and techniques described here enable partial reconstruction of heart dynamics from one-lead and multiple-lead systems, and can allow a cardiac monitoring system to accurately locate fiducial points such as P-wave onset, P-wave offset, T-wave onset, T-wave offset, Q-point, R-point, and S-point. Moreover, the system can assist in detecting a physiological condition, such as ventricular fibrillation, premature ventricular contraction (PVC), heart block conditions, long QT syndrome or QT prolongation, etc. Clinically, it can be very important to accurately identify the location of fiducial points. For example, accurate identification of fiducial points can be important in the calculation of the PR or QT intervals. Small variations of even 5 ms of the QT interval can be significant. Reconstructing the dynamics of the heart from the ECG signals can result in more accurate analysis of the heart's activity. The systems and techniques below can result in improved analysis without requiring significant additional computational resources.

Figure 1:
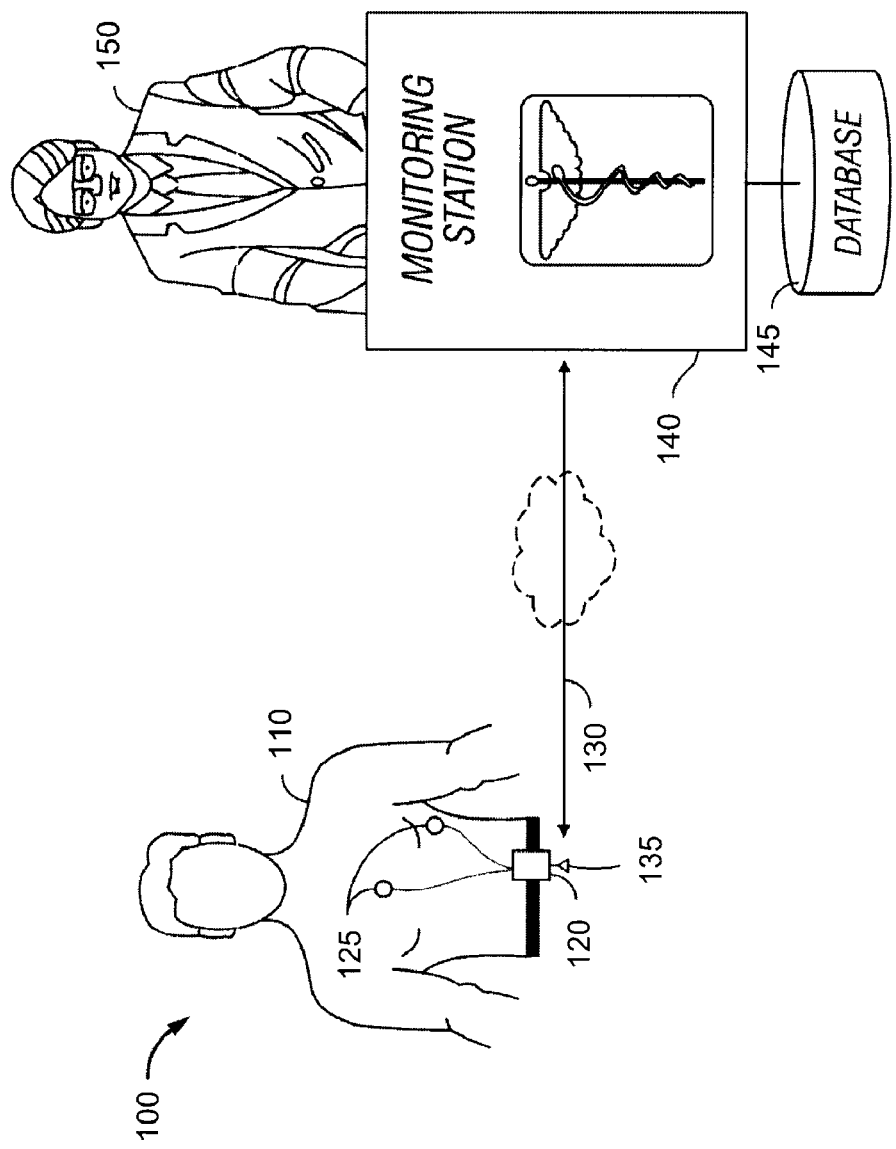
FIG. 1 shows a cardiac monitoring system in which a cardiac signal is monitored for medical purposes.

FIG. 1 shows a cardiac monitoring system 100 in which a cardiac signal is monitored for medical purposes. A patient 110 (e.g., a human patient, including potentially a healthy patient for whom cardiac monitoring is nonetheless deemed appropriate) has a cardiac monitoring apparatus 120 configured to obtain cardiac signals from the patient's heart. The cardiac monitoring apparatus 120 can be composed of one or more devices, such as a processing device and a sensing device. The sensing device can include one or more leads 125, which can receive electrical signals through body surface electrodes. These leads (as shown, for example, two leads e.g., silver/silver chloride electrodes) can be positioned at defined locations to aid in monitoring the electrical activity of the heart. As used herein, the term "lead" should be understood as including both a device that is subject to a potential difference that yields a voltage signal, such as an electrode that produces an ECG signal, and a conductor that forms a signal path to the apparatus 120 (e.g. to a signal amplifier in the apparatus 120).

The cardiac monitoring apparatus 120 can communicate with a monitoring station 140 (e.g., a computer in a monitoring center) via a communications channel 130. The cardiac monitoring apparatus 120 can include one or more sensing, calibration, signal processing, control, data storage, and transmission devices suitable for generating and processing the cardiac signal, as well as for relaying all or a portion of the cardiac signal over the communications channel 130. The communications channel 130 can be part of a communications network and can include any suitable medium for data transmission, including wired and wireless media suitable for carrying optical and/or electrical signals. Wireless communications by the apparatus 120 can employ a suitable antenna 135 as illustrated.

The cardiac monitoring apparatus 120 can communicate sensed cardiac signals, cardiac event information (e.g., real-time heart rate data), and additional physiological and/or other information to the monitoring station 140. The cardiac monitoring apparatus 120 can include an implantable medical device, such as an implantable cardiac defibrillator and an associated transceiver or pacemaker and an associated transceiver, or an external monitoring device that the patient wears or that is installed near the patient. Moreover, the cardiac monitoring apparatus 120 can be implemented using, for example, the CardioNet Mobile Cardiac Outpatient Telemetry (MCOT) device, which is commercially available and provided by CardioNet, Inc. of San Diego, Calif.

The monitoring station 140 can include a receiver element for receiving transmitted signals, as well as various data processing and storage elements for extracting and storing information carried by transmissions regarding the state of the patient 110. The monitoring station 140 can be located in the same general location (e.g., in the same room, building or health care facility) as the monitoring apparatus 120, or at a remote location. The monitoring station 140 can include a display and a processing system. A system operator 150 (e.g., a health care provider such as a doctor or a cardiovascular technician) can use the monitoring station 140 to evaluate physiological data received from the cardiac monitoring apparatus 120. The system operator 150 can use the monitoring station 140 to change operational settings of the cardiac monitoring apparatus 120 remotely during active cardiac monitoring of the patient 110.

Moreover, the cardiac monitoring apparatus 120 and/or the monitoring station 140 can use the systems and techniques described herein to identify physiological information concerning the patient 110. This can include signal processing and analysis on both an actively received signal (which can be cached in memory at the station 140) and prior signals stored in a storage medium or device such as in a database 145. For example, historical signal information for a person can be used in conjunction with the systems and techniques described herein to improve analysis of currently acquired signals, and can facilitate heart beat classification and characterization of physiological conditions, which can assist a clinician or physician in making an appropriate diagnosis and prescribing an appropriate treatment.

Figure 2A:
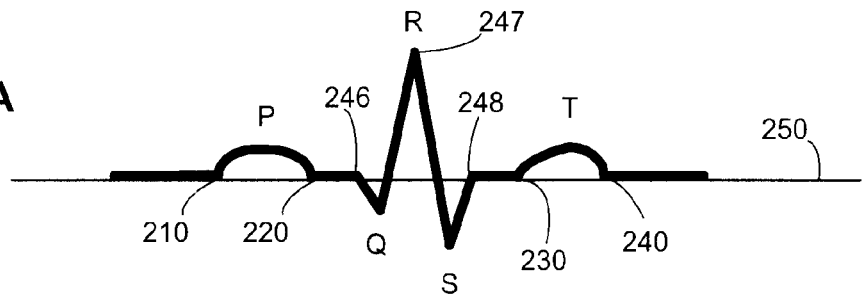
FIGS. 2A-2E show various graphical representations of ECG signals.
Figure 2B:
Figure 2C:
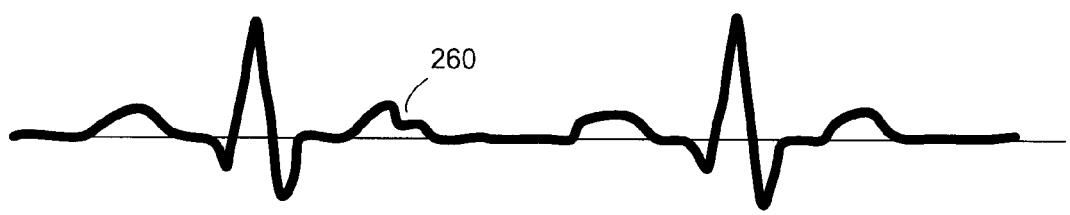
Figure 2D:
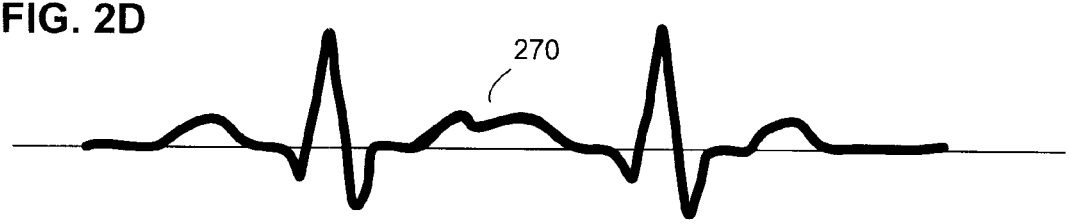
Figure 2E:
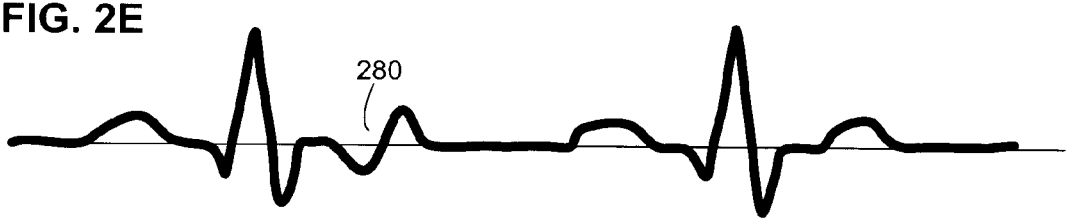

FIGS. 2A-2E show various graphical representations of ECG signals. FIG. 2A shows a graphical representation of a normal ECG signal. As shown, portions of an ECG signal have been identified using the conventional lettering: P, Q, R, S, and T (e.g. P identifies the P-wave, and T identifies the T-wave etc.). Isoelectric line 250 represents the baseline voltage of the ECG signal. Various fiducial points can be identified on the ECG signal. For example, the P-wave has a P-wave onset 210 and a P-wave offset 220. In like manner, the T-wave has a T-wave onset 230 and a T-wave offset 240. Other fiducial points can include, for example, a Q-point 246 which is the beginning of ventricular depolarization, an R-point 247 which is the peak of the QRS complex, and an S-point 248 which is the end of ventricular depolarization. In FIG. 2, these onsets and offsets occur along the isoelectric line 250. In practice, however, traditional approaches to identification of the fiducial points and the isoelectric line can be affected by various physiological factors such as by baseline wandering (FIG. 2B), T-U wave collision 260 (FIG. 2C), T-P wave collision 270 (FIG. 2D), abnormal T-wave such as an inverted signal 280 (FIG. 2E), etc.

Figure 3:
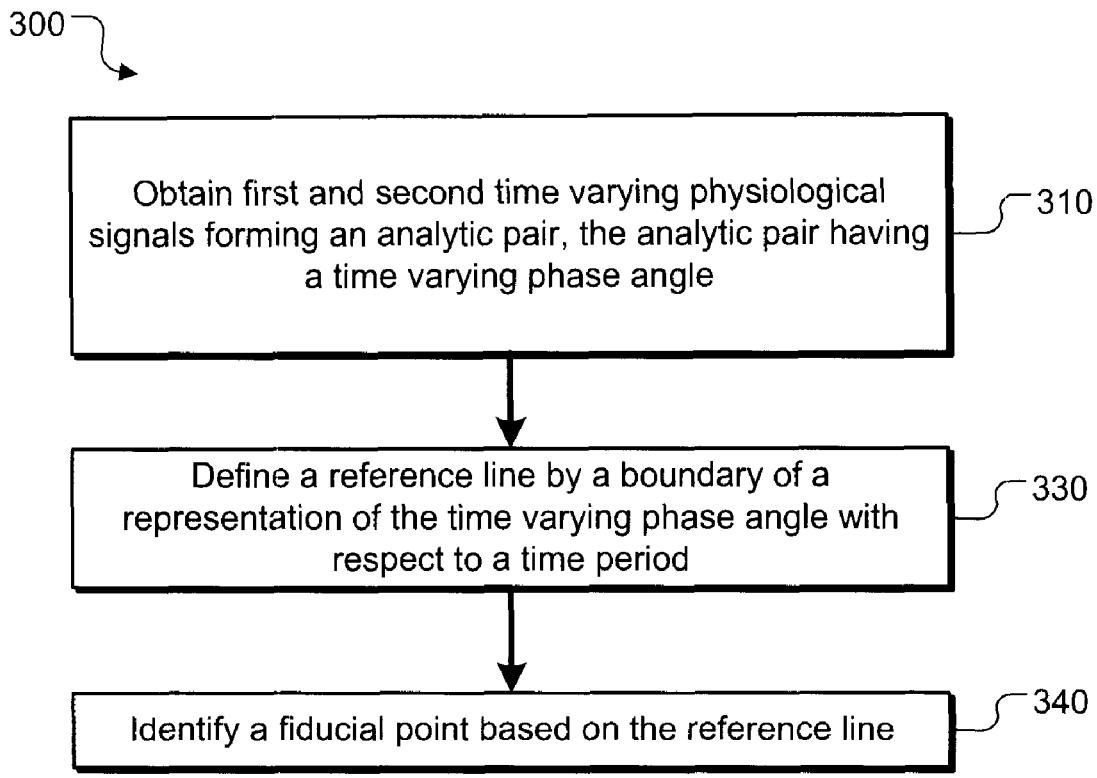
FIG. 3 shows an example procedure for identifying fiducial points.

FIG. 3 shows an example procedure 300 for identifying fiducial points. At 310, first and second time varying signals related to biological activity of an organism are obtained. The time varying signals can be any two vectors related to biological activity that have a time varying phase angle. The first time varying signal can be denoted by x(t). The second time varying signal is also related to the same biological activity of the organism as the first time varying signal and can be denoted by x̂(t). The first and second time varying signals form an analytic pair, which can be denoted by $\vec{A}(t)$. The analytic pair has a time varying phase angle, which can be denoted by $\vec{\phi}(t)$. The first and second time varying signals can be obtained in real-time (subject to communication and caching delays) or obtained from a storage device. Based on a phase property of a time varying phase angle of such an analytic pair, a representation of time vary phase angle with respect to time will have a mathematically defined boundary.

In some examples, the first and second time varying signals can be sensed ECG signals representative of a cardiac activity of a patient. For example, a multiple lead configuration can be used such that a second time varying signal can be a sensed ECG signal for the same cardiac activity as the first time varying ECG signal but obtained from a different lead field. The multiple lead configuration can be configured such that the sensed second time varying ECG signal is generally orthogonal to the sensed first time varying ECG signal. One such multiple lead configuration is the Frank electrocardiographic lead system which can achieve, to a good approximation, lead vectors that are mutually orthogonal. The first time varying signal can be obtained from one of these mutually orthogonal vectors and the second time varying signal can be obtained from another of these mutually orthogonal vectors.

In other examples, the second time varying signal can be obtained by obtaining a transformation of the first time varying signal. The transformation of x(t) can be a derivative (e.g. first derivative (d/dx), second derivative ($d^2/dx^2$), etc.) of the function x(t). The transformation of x(t) can be a Hilbert transform, H(x(t)). Other transforms can be obtained as well, such as a trigonometric function of x(t), Laplace transform of x(t), a Fourier transform of x(t), etc.

The time varying, phase angle of the analytic pair can be approximated by computing the changes of $\vec{A}(t)$, where x̂(t) is the second time varying signal (which can be a transformation of x(t)), where i is the current sample, where K is K samples away, and where $\Delta\vec{A}(t_{i+K})$ is the change of the two vectors $((x(t_i),x̂(t_i))$ and $(x(t_{i+K}),x̂(t_{i+K}))$. An approximation of the time varying phase angle, $\phi_{\Delta\vec{A}(t_{i+K})}$, can be defined by the function:

$$\frac{imag[\Delta\vec{A}(t_{i+K})]}{|\Delta\vec{A}(t_{i+K})|} = \frac{x̂(t_{i+K}) - x̂(t_i)}{\sqrt{(x(t_{i+K}) - x(t_i))^2 + (x̂(t_{i+K}) - x̂(t_i))^2}} \approx \varphi_{\Delta\vec{A}(t_{i+K})}$$

At 330, a reference line is defined by a boundary of a representation of the time varying phase angle with respect to a time period. The time period can be the time period for a portion of the ECG signal that is being examined. Mathematically, a time varying phase or angular change does not involve an amplitude component therefore the lower boundary of a representation of the time varying phase angle with respect to time is not affected by baseline wandering. The representation of the time varying phase angle can include, for example, a plot of the time varying phase angle with respect to the time period. The representation of the time varying phase angle can also include an approximation of the time varying phase angle with respect to the time period. Because the phase changes are bounded by $$[2k\pi - \frac{\pi}{2}, 2k\pi + \frac{\pi}{2}],$$

the plot of the time varying phase angle or an approximation of the time varying phase angle with respect to the time period is bound by $$[-\frac{\pi}{2}, \frac{\pi}{2}]$$

(or in degrees [−90°, 90°]). In this case, a reference line, such as an isoelectric line can be defined by the lower boundary, y=−π/2. A reference line can also be defined by the upper bounder y=−π/2. The representation can also be created by applying a trigonometric function to the time varying phase angle or an approximation of the time varying phase angle for the time period. In which case, the time varying phase angle is bounded by [−1, 1] and the reference line can be defined by the lower boundary y=−1, or the upper boundary y=1.

At 340, a fiducial point can be identified based on the reference line. In some examples, the time varying phase angle can be represented by a series of data points rather than a continuous line. A fiducial point can be identified at the time that corresponds to the point that comes closest to or intersects with the reference line. For example, when determining a fiducial point along the isoelectric line such as offset or onset, the fiducial point can be identified as the time associated with the point on the representation of the time varying phase angle that comes closest to or intersects with the reference line along the lower boundary. Or for example, a peak of an ECG signal, such as an R-point, P-peak, or a T-peak can be identified at the time associated with the point on the representation of the of the time varying phase angle that comes closest to or intersects with the reference line along the upper boundary.

In other examples, the fiducial point can be identified based on an intersection of a reference line with a corresponding function to a downslope or an upslope of the representation of the time varying phase angle. For example, a corresponding function can be a line or curve calculated for a downslope or an upslope of the representation. A corresponding function can be calculated for the downslope of a T-wave. A T-wave offset can be identified based on the intersection of the corresponding function with the reference line along the lower boundary of the representation of the time varying phase angle. A T-wave peak can be identified based on the intersection of the corresponding function with the reference line along the upper boundary of the representation of the time varying phase angle. In like manner, for a T-wave onset, a corresponding function can be calculated for the upslope of a T-wave. And, for a P-wave offset, a corresponding function can be calculated for a downslope of a P-wave. For a P-wave onset, a corresponding function can be calculated for an upslope of a P-wave.

Various methods can be used to calculate a corresponding function to a downslope or an upslope of the representation of the time varying phase angle. For example, when identifying an offset, calculating the corresponding function can include calculating the line tangent to the point where the downslope has a minimum slope. When identifying an onset, calculating the corresponding function can include calculating the line tangent to the point where the upslope has a maximum slope. In some examples, the corresponding function can be the regression line of a downslope or an upslope, $y=y_0=SLOPE_{regression}\cdot(x-x_0)$. Also, a least square fitting can be applied around the region where a downslope has a maximum slope or around the region where an upslope has a maximum.

An intersection of the corresponding function and the reference line is identified in order to determine a fiducial point. Identifying a fiducial point based on an intersection of the corresponding function can include offsetting the intersection of the corresponding function with the reference line by a constant. The constant can be determined using an average variation of detected values of like intersections from the true fiducial point. For example, over time, it can be determined by the monitoring apparatus, or some other automated apparatus, or by a medical profession that there is a variance between the actual fiducial point and the intersection of the corresponding function with the reference line. The measured intersection can be set-off by the average variance to identify the fiducial point. In some instances, mathematical transformations can impose a low pass filter effect moving the intersect of the corresponding function away from the true fiducial point. In such cases, the variation can be constant which can be calculated mathematically or by detection. Over time, the monitoring system can automatically or by feedback from a medical technician update the constant used to determine the fiducial points based on data received from monitoring a patient or patients. In some examples, offsetting the intersection may not be necessary when determining a fiducial point. For example, identifying an isoelectric line at the lower boundary of the representation of the time varying phase angle can provide consistency between measurements. So, offsetting the intersection may not be necessary when determining fiducial points for use in calculating dynamic changes of intervals such as $\Delta QT$.

Figure 4:
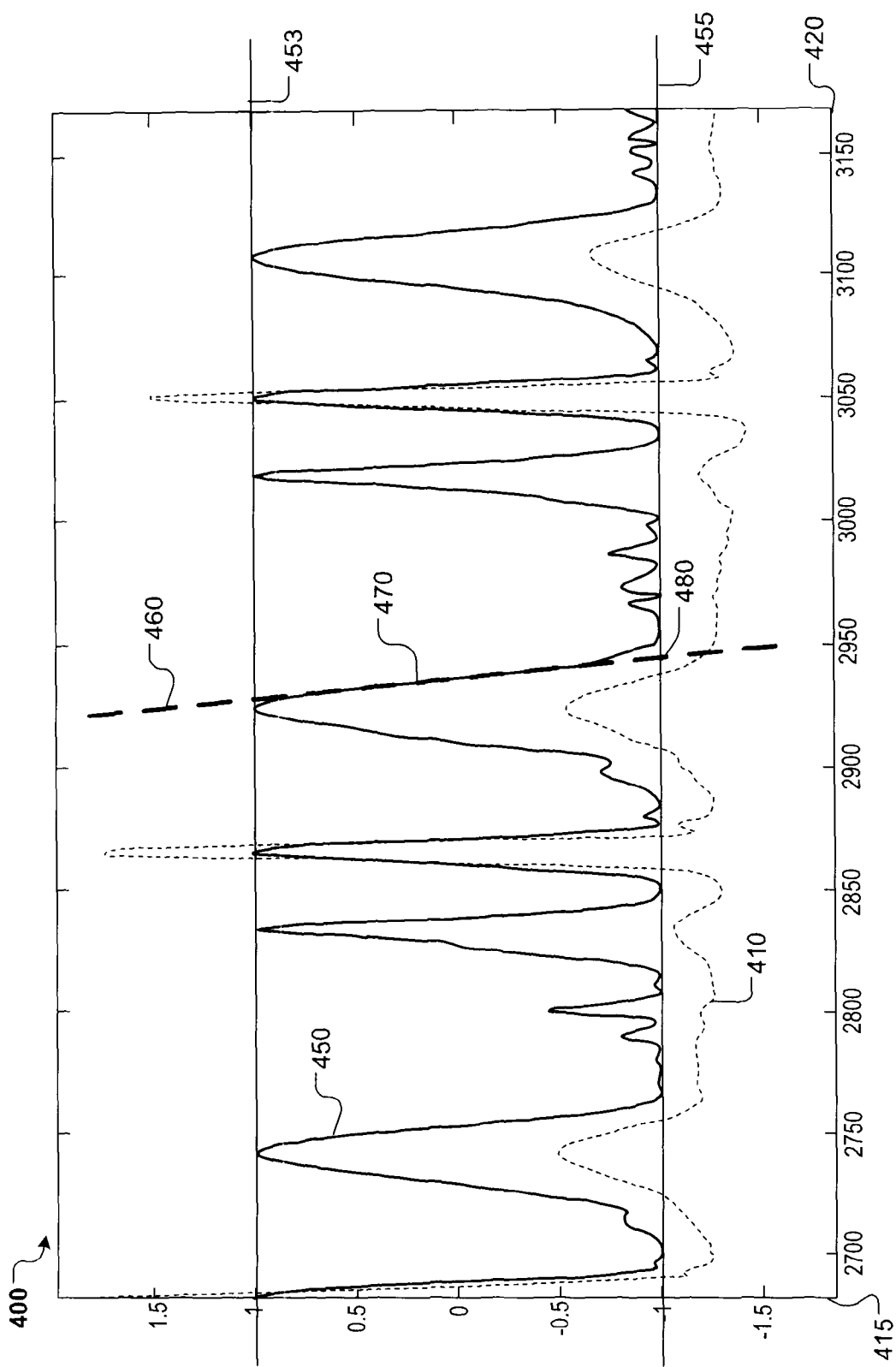
FIG. 4 shows a graphical representation of identification of a T-wave offset.

FIG. 4 shows a graphical representation of identification of a T-wave offset. Graph 400 shows a graphical representation of an ECG signal 410 and a graphical representation of a time-varying phase angle 450 for a given time period. Time is represented by the x-axis 420. The y-axis 415 represents both volts for the amplitude of the ECG signal 410 and a trigonometric value for the representation of the time varying phase angle 450. As can be seen, the ECG signal 410 is affected by base-line wandering. In this example, the ECG signal 410 is the first time varying signal of an analytic pair. The second time varying signal is a Hilbert transformation of the ECG signal. The analytic pair has a time varying phase angle, which is graphically represented by 450. The graphical representation of the time varying phase angle 450 is the trigonometric function of the time varying phase angle and has well defined positive and negative boundaries at $y=+/-1$. The graph 400 shows a graphical representation of the upper boundary 453 and the lower bounder 455. The reference line, $y=-1$, can be identified as the isoelectric line. The upper boundary, $y=1$ can also be identified as a reference line.

Graph 400 also shows a graphical representation of a corresponding function 460 to a downslope of the representation of the time varying phase angle that corresponds with a downslope of the T-wave. Corresponding function 460 is the tangent line to the point where the downslope has a minimum slope 470. The T-wave offset can be identified based on an intersection of the corresponding function 460 with the isoelectric line 455. A graphical representation of the intersection is shown at 480. Although FIG. 4 shows a graphical representation of how a fiducial point is determined, it by no means should be inferred that a graphical representation is necessary to identify a reference line or a fiducial point according to the methods and procedures described in this application. Such a determination can be done by a monitoring apparatus or the like without providing such a graphical representation. For example, a representation of the time varying phase angle with respect to a time period can be a set of data points representative of the time varying phase angle for a time period stored in a storage device. Although not graphically shown in FIG. 4, a representation similar the graphical representation of corresponding function 460 can also be used for identification of other fiducial points such as T-wave onset, P-wave offset, P-wave onset, Q-point, R-point, S-point, etc.

Figure 5:
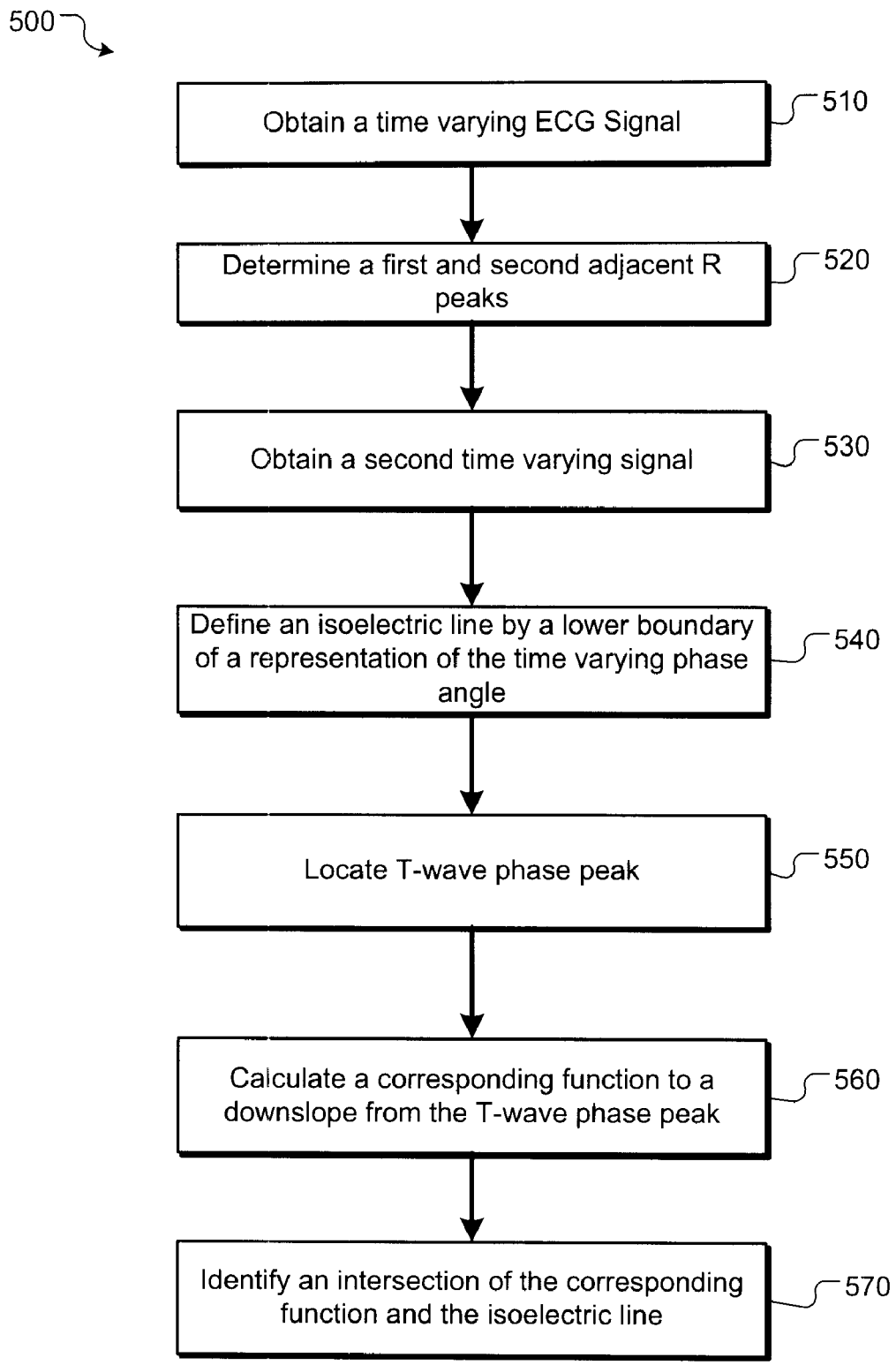
FIG. 5 shows an example procedure for identifying a T-wave offset.

FIG. 5 shows an example procedure 500 for identifying a T-wave offset. A procedure similar to the procedure in FIG. 5 can be performed for identification of other fiducial points. In FIG. 5 at 510, a time varying ECG signal is obtained. The ECG signal can be obtained real-time from a patient or from a data storage device. At 520, first and second adjacent R peaks are identified. At 530, a second time varying signal is obtained for a time period between the first and second R peaks (between $t=R[i]$ and $t=R[i+1]$), the first and second time varying phase angles forming an analytic pair. In some examples, the second time varying signal can be obtained by applying a transformation to portion of the ECG signal between the first and second R peak. In other examples, the second time varying signal can be obtained for the time period between the first and second R peaks from an ECG signal obtained from a different leads configuration than was used to obtain for the first time varying ECG signal.

At 540, an isoelectric line is defined by the lower boundary of a representation of the time varying phase angle with respect to the time period between the first and second R peaks. At 550, a T-wave phase peak is located between the first and second peaks using a preset algorithm. The preset algorithm can include for example locating a maximum phase peak between the time period: $t=R[i]+80$ ms and $t=R[i]+70\%$ $R[i]R[i+1]$. At 560, a corresponding function to a downslope from the T-wave phase peak is calculated. At 570, the intersection of the corresponding function with the isoelectric line is identified. Based on the intersection, the T-wave offset is identified. The intersection itself can be identified as the T-wave offset. In other examples, the intersection can be altered by a pre-set amount to determine the T-wave offset.

The disclosed systems, techniques, and all of the functional operations described and illustrated in this specification can be implemented in digital electronic circuitry, or in computer hardware, firmware, software, or in combinations of the forgoing. For example, one or more computers and/or circuitry can be operable to or configured and arranged to perform the functions and techniques disclosed herein. Apparatuses and/or systems can be implemented using a software product (e.g., a computer program product) tangibly embodied in a machine-readable storage device for execution by a programmable processor, and processing operations can be performed by a programmable processor executing a program of instructions to perform functions by operating on input data and generating output. Further, the system can be implemented advantageously in one or more software programs that are executable on a programmable system. This programmable system can include the following: 1) at least one programmable processor coupled to receive data and instructions from, and to transmit data and instructions to, a data storage system; 2) at least one input device; and 3) at least one output device. Moreover, each software program can be implemented in a high-level procedural or object-oriented programming language, or in assembly or machine language if desired; and in any case, the language can be a compiled or an interpreted language.

Also, suitable processors include, by way of example, both general and special purpose microprocessors. Generally, a processor will receive instructions and data from a read-only memory, a random access memory, and/or a machine-readable signal (e.g., a digital signal received through a network connection). The essential elements of a computer are a processor for performing instructions and one or more memory devices for storing instructions and data. Generally, a computer will include one or more mass storage devices for storing data files. Such devices can include magnetic disks, such as internal hard disks and removable disks, magneto-optical disks, and optical disks. Storage devices suitable for tangibly embodying software program instructions and data include all forms of non-volatile memory, including, by way of example, the following: 1) semiconductor memory devices, such as EPROM (electrically programmable read-only memory); EEPROM (electrically erasable programmable read-only memory) and flash memory devices; 2) magnetic disks such as internal hard disks and removable disks; 3) magneto-optical disks; and 4) CD-ROM disks. Any of the foregoing can be supplemented by, or incorporated in, ASICs (application-specific integrated circuits).

The disclosed systems and techniques, described and illustrated in this specification can be implemented using a communications network such as a wired or wireless network. Examples of communication networks include, e.g., a local area network ("LAN"), a wide area network ("WAN"), the Internet or any combinations of such.

To provide for interaction with a user (such as the health care provider), the system can be implemented on a computer system having a display device such as a monitor or LCD (liquid crystal display) screen for displaying information to the user and a keyboard and a pointing device such as a mouse or a trackball by which the user can provide input to the computer system. The computer system can be programmed to provide a graphical user interface through which computer programs interact with users.

A number of embodiments of the invention have been described. Nevertheless, it will be understood that various modifications may be made without departing from the spirit and scope of the invention. For example, the disclosed operations can be performed in a different order and still achieve desirable results. Accordingly, other embodiments are within the scope of the following claims.

What is claimed is:

1. A machine implemented method comprising:
    obtaining a first time varying physiological signal and a second time varying physiological signal that relate to biological activity of an organism, the first time varying physiological signal and the second time varying physiological signal forming an analytic pair wherein the analytic pair has a time varying phase angle;
    defining a reference line by a boundary of a representation of the time varying phase angle with respect to a time period; and
    identifying a fiducial point based on the reference line.

2. The machine implemented method of claim 1, further comprising approximating the time varying phase angle, wherein the approximation of the varying phase angle $\phi_{\Delta \vec{A}(t_{i+K})}$ is defined by the function:

$$\varphi_{\Delta \vec{A}(t_{i+K})} \approx \frac{imag[\Delta \vec{A}(t_{i+K})]}{|\Delta \vec{A}(t_{i+K})|} = \frac{\hat{x}(t_{i+K}) - \hat{x}(t_i)}{\sqrt{(x(t_{i+K}) - x(t_i))^2 + (\hat{x}(t_{i+K}) - \hat{x}(t_i))^2}}$$

where x(t) comprises the first time varying physiological signal and $\hat{x}(t)$ comprises the second time varying physiological signal, x(t) and $\hat{x}(t)$ forming the analytic pair $\vec{A}(t)$; where i is a current sample; where K is K samples away; and where $\Delta \vec{A}(t_{i+k})$ is the change of the two vectors ($(x(t_i), \hat{x}(t_i))$) and $(x(t_{i+K}), \hat{x}(t_{i+K}))$).

3. The machine implemented method of claim 1, wherein the reference line comprises an isoelectric line defined by a lower boundary of the representation of the time varying phase angle.

4. The machine implemented method of claim 1, further comprising:
    calculating a corresponding function to a downslope or an upslope of the representation of the time varying phase angle within the time period; and
    wherein identifying a fiducial point based on the reference line comprises identifying a fiducial point based on an intersection of the corresponding function and the reference line.

5. The machine implemented method of claim 4, wherein calculating a corresponding function to a downslope of the representation of the time varying phase angle comprises calculating a tangent line where the downslope has a minimum slope.

6. The machine implemented method of claim 4, wherein calculating a corresponding function to an upslope of the representation of the time varying phase angle comprises calculating a tangent line where the upslope has a maximum slope.

7. The machine implemented method of claim 4, wherein identifying a fiducial point based on an intersection of the corresponding function and the reference line comprises offsetting the intersection by a constant.

8. The machine implemented method of claim 4, wherein calculating a corresponding function to a downslope or an upslope of the representation of the time varying phase angle comprises calculating the regression line of the downslope or the upslope of the representation of the time varying phase angle within the time period.

9. The machine implemented method of claim 1, comprising applying a trigonometric function to the time varying phase angle to create the representation.

10. The machine implemented method of claim 1,
    wherein obtaining a first time varying physiological signal comprises obtaining a sensed signal x(t); and
    wherein obtaining a second time varying physiological signal $\hat{x}(t)$ comprises obtaining a transformation of x(t) to form the analytic pair $\vec{A}(t)$.

11. The machine implemented method of claim 10, wherein obtaining a transformation of x(t) comprises obtaining a Hilbert Transformation H(x(t)) of the first time varying physiological signal.

12. The machine implemented method of claim 10, wherein obtaining a transformation of x(t) comprises obtaining a derivative of x(t).

13. The machine implemented method of claim 1,
wherein obtaining a first time varying physiological signal comprises obtaining a first sensed signal based on a first lead configuration;
wherein obtaining a second time varying physiological signal comprises obtaining a second sensed signal based on a second lead configuration wherein the second sensed signal is orthogonal to the first; and
wherein obtaining the first and second time varying physiological signals comprises obtaining the signals from a data storage device.

14. The machine implemented method of claim 1, wherein identifying a fiducial point comprises identifying one of a T-wave offset, T-wave onset, P-wave offset, P-wave onset, Q-point, R-point, and S-point.

15. A system comprising:
one or more computers; and
a computer-readable storage device having a computer program product encoded therein, the computer program product operable to cause the one or more computers to perform operations comprising:
obtaining a first time varying physiological signal and a second time varying physiological signal that relate to biological activity of an organism, the first time varying physiological signal and the second time varying physiological signal forming an analytic pair wherein the analytic pair has a time varying phase angle;
defining a reference line by a boundary of a representation of the time varying phase angle with respect to a time period; and
identifying a fiducial point based on the reference line.

16. The system of claim 15, wherein the computer-readable storage device is further operable to cause the one or more computers to perform operations comprising:
calculating a corresponding function to a downslope or an upslope of the representation of the time varying phase angle within the time period; and
wherein identifying a fiducial point based on the reference line comprises identifying a fiducial point based on an intersection of the corresponding function and the reference line.

17. The system of claim 16, wherein calculating a corresponding function to a downslope or an upslope of the representation of the time varying phase angle comprises calculating one of a tangent line, a regression line, and a least square approximation to the downslope or the upslope.

18. The system of claim 16, wherein identifying a fiducial point based on an intersection of the corresponding function and the reference line comprises offsetting the intersection by a constant.

19. The system of claim 15, wherein the computer-readable storage device is further operable to cause the one or more computers to perform operations comprising:
applying a trigonometric function to the time varying phase angle to create the representation.

20. The system of claim 15, wherein the computer-readable storage device is further operable to cause the one or more computers to perform operations comprising:
approximating the time varying phase angle, wherein the approximation of the varying phase angle $\phi_{\Delta \vec{A}(t_{i+K})}$ is defined by the function:

$$\varphi_{\Delta \dot{A}(t_{i+K})} \approx \frac{imag[\Delta \vec{A}(t_{i+K})]}{|\Delta \vec{A}(t_{i+K})|} = \frac{\hat{x}(t_{i+K}) - \hat{x}(t_i)}{\sqrt{(x(t_{i+K}) - x(t_i))^2 + (\hat{x}(t_{i+K}) - \hat{x}(t_i))^2}}$$

where x(t) comprises the first time varying physiological signal and x̂(t) comprises the second time varying physiological signal, x(t) and x̂(t) forming the analytic pair $\vec{A}(t)$; where i is a current sample; where K is K samples away; and where $\Delta \vec{A}(t_{i+k})$ is the change of the two vectors ((x(t_i),x̂(t_i)), and (x(t_{i+K}),x̂(t_{i+K})).

21. The system of claim 15,
wherein obtaining a first time varying physiological signal comprises obtaining a sensed signal x(t); and
wherein obtaining a second time varying physiological signal x̂(t) comprises obtaining a transformation of x(t) to form the analytic pair $\vec{A}(t)$.

22. The system of claim 21, wherein obtaining a transformation of x(t) comprises obtaining a Hilbert Transformation H(x(t)) of the first time varying physiological signal.

23. The system of claim 21, wherein obtaining a transformation of x(t) comprises obtaining a derivative of x(t).

24. The system of claim 15, wherein obtaining a first time varying physiological signal comprises obtaining a first sensed signal based on a first lead configuration;
wherein obtaining a second time varying physiological signal comprises obtaining a second sensed signal based on a second lead configuration wherein the second sensed signal is orthogonal to the first; and
wherein obtaining the first and second time varying physiological signals comprises obtaining the signals from a data storage device.

25. The system of claim 15, wherein identifying a fiducial point comprises identifying one of a T-wave offset, T-wave onset, P-wave offset, P-wave onset, Q-point, R-point, and S-point.

26. An apparatus comprising:
circuitry operable to obtain a first time varying physiological signal and a second time varying physiological signal that relate to biological activity of an organism, the first time varying physiological signal and the second time varying physiological signal forming an analytic pair wherein the analytic pair has a time varying phase angle;
circuitry operable to define a reference line by a boundary of a representation of the time varying phase angle with respect to a time period; and
circuitry operable to identify a fiducial point based on the reference line.

27. The apparatus of claim 26, further comprising
circuitry operable to transmit the identified fiducial points.

28. The apparatus of claim 26, further comprising
circuitry operable to calculate a corresponding function to a downslope or an upslope of the representation of the time varying phase angle within the time period; and
wherein the circuitry operable to identify a fiducial point is further operable to identify a fiducial point based on an intersection of the corresponding function and the reference line.

29. The apparatus of claim 28, wherein the circuitry operable to calculate a corresponding function to a downslope or an upslope of the representation of the time varying phase angle is further operable to calculate one of a tangent line, a regression line, and a least square approximation to the downslope or the upslope.

30. The apparatus of claim 28, wherein the circuitry operable to identify a fiducial point based on an intersection of the corresponding function and the reference line is further operable to offset the intersection by a constant.

31. The apparatus of claim 26,
further comprising circuitry operable to approximate the time varying phase angle, wherein the approximation of the varying phase angle $\phi_{\Delta\vec{A}(t_{i+K})}$ is defined by the function:

$$\varphi_{\Delta\vec{A}(t_{i+K})} \approx \frac{imag[\Delta\vec{A}(t_{i+K})]}{|\Delta\vec{A}(t_{i+K})|} = \frac{\hat{x}(t_{i+K}) - \hat{x}(t_i)}{\sqrt{(x(t_{i+K}) - x(t_i))^2 + (\hat{x}(t_{i+K}) - \hat{x}(t_i))^2}}$$

where x(t) comprises the first time varying physiological signal and x̂(t) comprises the second time varying physiological signal, x(t) and x̂(t) forming the analytic pair $\vec{A}(t)$; where i is a current sample; where K is K samples away; and where $\Delta\vec{A}(t_{i+k})$ is the change of the two vectors ((x(t$_i$),x̂(t$_i$)) and (x(t$_{i+K}$),x̂(t$_{i+K}$))).

32. The apparatus of claim 26, further comprising circuitry operable to apply a trigonometric function to the time varying phase angle to create the representation.

33. The apparatus of claim 26,
wherein the circuitry operable to obtain a first time varying physiological signal is further operable to obtain a sensed signal x(t); and
wherein the circuitry operable to obtain a second time varying physiological signal x̂(t) is further operable to obtain a transformation of x(t) to form the analytic pair $\vec{A}(t)$.

34. The apparatus of claim 33, wherein the circuitry operable to obtain a transformation of x(t) is further operable to obtain a Hilbert Transformation H(x(t)) of the first time varying physiological signal.

35. The apparatus of claim 33, wherein the circuitry operable to obtain a transformation of x(t) comprises obtaining a derivative of x(t).

36. The apparatus of claim 26,
wherein the circuitry operable to obtain a first time varying physiological signal is further operable to obtain a first sensed signal based on a first lead configuration;
wherein the circuitry operable to obtain a second time varying physiological signal is further operable to obtain a second sensed signal based on a second lead configuration wherein the second sensed signal is orthogonal to the first; and
wherein the circuitry operable to obtain the first and second time varying physiological signals is further operable to obtain the signals from a data storage device.

37. The apparatus of claim 26, wherein the circuitry operable to identify a fiducial point is further operable to identify one of a T-wave offset, T-wave onset, P-wave offset, P-wave onset, Q-point, R-point, and S-point.

* * * * *

UNITED STATES PATENT AND TRADEMARK OFFICE
CERTIFICATE OF CORRECTION

PATENT NO.       : 8,200,319 B2                                        Page 1 of 3
APPLICATION NO.  : 12/368976
DATED            : June 12, 2012
INVENTOR(S)      : Yachuan Pu It is certified that error appears in the above-identified patent and that said Letters Patent is hereby corrected as shown below:

IN THE SPECIFICATIONS:

At Column 1, Line 50:

delete " $\phi_{\Delta \vec{A}}(t_{j+K})$ " and insert -- $\varphi_{\Delta \vec{A}(t_{j+K})}$ --, therefor.

At Column 3, Line 10:

delete " $\phi_{\Delta \vec{A}}(t_{j+K})$ " and insert -- $\varphi_{\Delta \vec{A}(t_{j+K})}$ --, therefor.

At Column 4, Line 10:

delete " $\phi_{\Delta \vec{A}}(t_{j+K})$ " and insert -- $\varphi_{\Delta \vec{A}(t_{j+K})}$ --, therefor.

At Column 7, Line 55:

delete " $\phi_{\Delta \vec{A}}(t_{j+K})$ " and insert -- $\varphi_{\Delta \vec{A}(t_{j+K})}$ --, therefor.

Signed and Sealed this
Sixteenth Day of October, 2012

David J. Kappos
*Director of the United States Patent and Trademark Office*

CERTIFICATE OF CORRECTION (continued)
U.S. Pat. No. 8,200,319 B2

IN THE CLAIMS:

At Column 12, Line 8:

In Claim 2, delete "$\phi_{\Delta\vec{A}(t_{i+K})}$" and insert -- $\varphi_{\Delta\vec{A}(t_{i+K})}$ --, therefor.

At Column 12, Line 20:

In Claim 2, delete "$\Delta\vec{A}(t_{i+k})$" and insert -- $\Delta\vec{A}(t_{i+K})$ --, therefor.

At Column 12, Line 20:

In Claim 2, delete "$((x(t_i), \hat{x}(t_i))$" and insert -- $(x(t_i), \hat{x}(t_i))$ --, therefor.

At Column 12, Line 21:

In Claim 2, delete "$(x(t_{i+K}), \hat{x}(t_{i+K}))$." and insert -- $(x(t_{i+K}), \hat{x}(t_{i+K}))$. --, therefor.

At Column 13, Line 53:
In Claim 18, delete "of 16" and insert -- of claim 16, -- therefor.

At Column 13, Line 66:

In Claim 20, delete "$\phi_{\Delta\vec{A}(t_{i+K})}$" and insert -- $\varphi_{\Delta\vec{A}(t_{i+K})}$ --, therefor.

At Column 14, Line 3:

In Claim 20, delete "$\varphi_{\Delta\dot{A}(t_{i+K})}$" and insert -- $\varphi_{\Delta\vec{A}(t_{i+K})}$ --, therefor.

At Column 14, Line 11:

In Claim 20, delete "$\Delta\vec{A}(t_{i+k})$" and insert -- $\Delta\vec{A}(t_{i+K})$ --, therefor.

CERTIFICATE OF CORRECTION (continued)
U.S. Pat. No. 8,200,319 B2

At Column 14, Line 11:

In Claim 20, delete "$((x(t_i), \hat{x}(t_i)),$" and insert -- $(x(t_i), \hat{x}(t_i))$ --, therefor.

At Column 15, Line 19:

In Claim 31, delete "$\Delta \vec{A}(t_{i+k})$" and insert -- $\Delta \vec{A}(t_{i+K})$ --, therefor.

At Column 15, Line 19:

In Claim 31, delete "$((x(t_i), \hat{x}(t_i))$" and insert -- $(x(t_i), \hat{x}(t_i))$ --, therefor.